US011471534B2

(12) United States Patent
Choi et al.

(10) Patent No.: US 11,471,534 B2
(45) Date of Patent: Oct. 18, 2022

(54) CHITOSAN-PLURONIC COMPLEX AND NANO-CARRIER COMPRISING SAME

(71) Applicants: KOREA INSTITUTE OF CERAMIC ENGINEERING AND TECHNOLOGY, Jinju-si (KR); SKINMED CO., LTD., Daejeon (KR)

(72) Inventors: Won Il Choi, Seoul (KR); Sung Hyun Kim, Sejong (KR); Yong Chul Shin, Jinju-si (KR); Jeung Hoon Lee, Daejeon (KR); Jin Hwa Kim, Daejeon (KR); Young Sung Yun, Jinju-si (KR)

(73) Assignee: SKINMED CO., LTD., Daejeon (KR)

( * ) Notice: Subject to any disclaimer, the term of this patent is extended or adjusted under 35 U.S.C. 154(b) by 83 days.

(21) Appl. No.: 16/624,994

(22) PCT Filed: Jun. 14, 2018

(86) PCT No.: PCT/KR2018/006706
§ 371 (c)(1),
(2) Date: Dec. 20, 2019

(87) PCT Pub. No.: WO2018/236090
PCT Pub. Date: Dec. 27, 2018

(65) Prior Publication Data
US 2020/0222542 A1    Jul. 16, 2020

(30) Foreign Application Priority Data

Jun. 21, 2017  (KR) .................. 10-2017-0078481

(51) Int. Cl.
| | | |
|---|---|---|
| *A61K 47/36* | (2006.01) | |
| *A61K 8/73* | (2006.01) | |
| *A61K 9/00* | (2006.01) | |
| *A61K 9/70* | (2006.01) | |
| *B82Y 5/00* | (2011.01) | |

(52) U.S. Cl.
CPC .............. *A61K 47/36* (2013.01); *A61K 8/736* (2013.01); *A61K 9/0019* (2013.01); *A61K 9/0053* (2013.01); *A61K 9/7023* (2013.01); *B82Y 5/00* (2013.01)

(58) Field of Classification Search
CPC ...... A61K 8/736; A61K 47/36; A61K 9/5146; A61K 9/5161; A61K 2800/10; A61K 2800/413; A61K 2800/56; A61K 2800/624; A61K 31/722; A61K 47/34; A61K 8/02; A61K 8/0279; A61K 8/11; A61K 8/73; A61K 8/84; A61K 8/90; A61K 9/00; A61K 9/0053; A61K 9/1273; A61K 9/7023; A61K 9/0014; A61K 9/0046; A61K 9/127; A61K 47/14; A61K 47/38; A61K 9/06; A61K 9/14; A61K 2039/505; A61K 31/05; A61K 31/13; A61K 31/137; A61K 31/325; A61K 31/43; A61K 31/436; A61K 31/519; A61K 31/5513; A61K 31/5517; A61K 38/18; A61K 38/1808; A61K 38/1825; A61K 38/185; A61K 38/1858; A61K 38/1883; A61K 41/0052; A61K 47/02; A61K 47/10; A61K 47/18; A61K 47/32; A61K 47/40; A61K 49/0093; A61K 9/0019; A61K 9/122; A61K 9/16; A61K 9/1647; A61K 9/5153; A61K 9/7007; A61K 31/00; A61K 31/135; A61K 31/24; A61K 31/27; A61K 31/44; A61K 31/444; A61K 31/496; A61K 31/498; A61K 31/522; A61K 31/5377; A61K 31/573; A61K 31/7036; A61K 31/724; A61K 38/05; A61K 45/06; A61K 47/20; A61K 47/28; A61K 47/30; A61K 47/46; A61K 47/61; A61K 8/042; A61K 8/23; A61K 8/26; A61K 9/0024; A61K 9/10; A61K 9/1641; A61P 17/00; A61P 25/02; A61P 25/22; A61P 27/16; A61P 29/00; A61P 31/04; A61P 35/00; A61P 37/02; A61P 37/06; A61P 43/00; C07K 16/241; C07K 2317/21; C07K 2317/76; A61Q 19/02; A61Q 19/08
See application file for complete search history.

(56) References Cited

U.S. PATENT DOCUMENTS

| | | | | |
|---|---|---|---|---|
| 2010/0016450 | A1* | 1/2010 | Lichter | ............... A61K 9/0019 |
| | | | | 514/772.1 |
| 2012/0087859 | A1* | 4/2012 | Tae | .................... A61K 49/0093 |
| | | | | 424/1.11 |

FOREIGN PATENT DOCUMENTS

| | | |
|---|---|---|
| CN | 102573923 A | 7/2012 |
| KR | 10-2013-0055847 A | 5/2013 |

(Continued)

OTHER PUBLICATIONS

Zhang, Wujie et al., Synthesis and characterization of thermally responsive pluronic F127-chitosan nanocapsules for controlled release and intracellular delivery of small molecules; ACS Nano, 2010, vol. 4; No. 11, pp. 6747-6759, provided by Applicant in IDS dated Dec. 20, 2019. (Year: 2010).*

(Continued)

*Primary Examiner* — Audrea B Coniglio
(74) *Attorney, Agent, or Firm* — Li & Cai Intellectual Property (USA) Office (57) ABSTRACT

The present invention relates to a transdermal nano-carrier and, more specifically, to a nano-carrier having a chitosan-based nano-sponge structure. According to the present invention, as a nano-carrier having enhanced transdermal delivery on the basis of a complex containing chitosan is provided, it is possible to effectively deliver drugs, cosmetic materials, etc. into the skin.

8 Claims, 5 Drawing Sheets

(56) References Cited

FOREIGN PATENT DOCUMENTS

| KR | 10-2014-0014579 A | 2/2014 |
|---|---|---|
| KR | 10-1607398 B1 | 3/2016 |

OTHER PUBLICATIONS

WIPO, International Search Report dated Feb. 7, 2019.
Wujie Zhang, et al., "Synthesis and Characterization of Thermally Responsive Pluronic F127-Chitosan Nanocapsules for Controlled Release and Intracellular Delivery of Small Molecules", ACS Nano, 2010, vol. 4, No. 11, pp. 6747-6759.
Hosseinzadeh Hosniyeh, et al., "Chitosan-Pluronic nanoparticles as oral delivery of anticancer gemcitabine: preparation and in vitro study", International Journal of Nanomedicine, 2012, vol. 7, pp. 1851-1863.
Ja-Young Kim, et al., "In-vivo tumor targeting of pluronic-based nano-carriers", journal of Controlled Release, pp. 109-117, Jun. 19, 2010.
Yong-Il Chung, et al., "The effect of surface functionalization of PLGA nanoparticles by heparin- or chitosan-conjugated Pluronic on tumor targeting", journal of Controlled Release, Jan. 25, 2010, pp. 374-382.
Wujie Zhang, et al., "Synthesis and Characterization of Thermally Responsive Pluronic F127-Chitosan Nanocapsule tor Controlled Release and Intracellular Delivery of Small Molecules", ACS Nano, Nov. 1, 2010, pp. 6747-6759.
European Patent Office, Extended European Patent Search report dated Nov. 12, 2020.
China Patent Office, Office action dated Apr. 30, 2021.

* cited by examiner

CHITOSAN-PLURONIC COMPLEX AND NANO-CARRIER COMPRISING SAME

BACKGROUND OF THE INVENTION

Field of the Invention

The present disclosure relates to a nanocarrier for transdermal penetration and, more particularly, provides a nanocarrier of a nanosponge structure based on chitosan.

Related Art

A drug that passes through the skin has an objective of allowing the drug to be delivered to a specific organ through the skin due by ease of its use. At the same time, a case of delivering an atopic dermatitis treatment agent, whitening cosmetics, cosmetics for wrinkle amelioration, or the like to the skin itself also exists.

The skin, as an organic having the largest surface area in the human body, becomes a path which is capable of effectively delivering a drug when an appropriate method is used. However, the skin has a difficulty in delivering materials which have large molecular weights and are hydrophilic since skin permeability of an external material is extremely low due to stratum corneum composed of dead cells at the outermost side of the skin. Particularly, this is true due to keratinocytes inside the stratum corneum and lipid between corneocytes between the keratinocytes. Molecules exhibiting physiological activities in most of the skin (hereinafter, referred to as skin's physiologically active molecules) have low percutaneous permeability rate due to resistance of the stratum corneum of the skin.

Various methods capable of promoting such a percutaneous permeability rate of the skin's physiologically active molecules have been studied, and much attention has recently been focused on a delivery system using a cell penetrating peptide. Use of a peptide having cell permeability has various advantages, and these advantages are mostly caused by various deformations which may be made in a peptide sequence at all times.

However, a delivery system using a peptide has had a problem that efficiency is lowered when connecting the delivery system with a biological active material to be delivered into the cells since the delivery system is likely to cause side effects such as an immune reaction and the like when the delivery system is applied to the human body, and may have influence on structure and function of protein to be delivered in that the delivery system selects and artificially synthesizes characteristic amino acid sequences through the analysis of amino acid sequences consisting of conventional cell penetrating peptides.

PRIOR ART DOCUMENT

Patent Document (Patent document 1) Korean Patent Laid-Open Publication No. 10-2012-0104036

SUMMARY OF THE INVENTION

The purpose of the present disclosure is to provide a nanocarrier which can be applied to cosmetic and pharmaceutical fields, has high biocompatibility, and is excellent in delivery of drug into the skin by providing a chitosan-including nanocarrier.

To achieve the purpose, a chitosan-pluronic complex in which chitosan is substituted at both ends of a pluronic polymer according to an aspect of the present disclosure is provided.

The pluronic polymer may be represented by the following chemical formula 1:

$(PEO)_a\text{-}(PPO)_b\text{-}(PEO)_a$     [Chemical Formula 1]

wherein the PEO is polyethylene oxide, the PPO is polypropylene oxide, and the a and b are each independently an integer of 1 to 300.

The chitosan may have a molecular weight of 3 to 760 kDa.

Furthermore, a nanocarrier comprising the chitosan-pluronic complex according to another aspect of the present disclosure is provided.

The nanocarrier may further comprise a pluronic polymer, and the chitosan-pluronic complex and the pluronic polymer may be mixed at such a weight ratio that 10 to 100 wt % of the chitosan-pluronic complex is mixed with 0 to 90 wt % of the pluronic polymer with respect to 100 wt % of the total weight of the chitosan-pluronic complex and the pluronic polymer.

Chitosan may have a molecular weight of 3 to 760 kDa in the chitosan-pluronic complex.

The nanocarrier may have a size of 500 nm or less, preferably 140 nm or less.

The nanocarrier may have a surface charge value of 0 to 50 mV, preferably 11 to 18 mV.

The nanocarrier may carry a drug or active ingredient having a low skin penetration rate, and the drug or active ingredient having the low skin penetration rate may have a loading efficiency of 90% or more. The drug or active ingredient having the low skin penetration rate may be a hydrophobic material, a hydrophilic material or a pharmaceutically acceptable material, and may include a high molecular weight material of which skin penetration is determined to be difficult.

The drug or active ingredient having the low skin penetration rate may be a functional material which is used in cosmetics, medicines, quasi-drugs or beauty products.

The nanocarrier may be used in the cosmetics, medicines, quasi-drugs or beauty products.

The nanocarrier may be a nanocarrier for transdermal penetration, oral administration, or invasion.

The nanocarrier may be used in a drug complex containing the drug or active ingredient having the low skin penetration rate.

Furthermore, a method of manufacturing a nanocarrier according to another aspect of the present disclosure is provided. The method comprises the steps of: (a) mixing a pluronic polymer with chitosan to prepare a complex in which chitosan is substituted at an end of the pluronic polymer; (b) mixing the complex with the pluronic polymer in the presence of a solvent to prepare a mixture; (c) dropping the mixture on distilled water; and (d) stirring the mixture-dropped distilled water.

The step (a) may comprise mixing chitosan with a molecular weight of 3 to 760 kDa.

The step (b) may comprise mixing the complex with the pluronic polymer such that 10 to 100 wt % of the chitosan-pluronic complex is mixed with 0 to 90 wt % of the pluronic polymer with respect to 100 wt % of the total weight of the chitosan-pluronic complex and the pluronic polymer.

DESCRIPTION OF EXEMPLARY EMBODIMENTS

Hereinafter, the present disclosure will be described in more detail through Examples. It will be obvious to a person having ordinary skill in the art that these examples are illustrative purposes only and are not to be construed to limit the scope of the present disclosure.

Example 1. Introducing a Reaction Group at Both End Groups of a Pluronic Polymer A reaction was performed on 323 mg of p-NPC (p-nitrophenyl chloroformate, 10 molar ratio) having excellent reactivity with amine at ends of 2 g of a polymer of Pluronic (Pluronic F127, (PEO)$_a$-(PPO)$_b$-(PEO)$_a$; the a and b are each independently an integer of 1 to 300) in 30 ml of dichloromethane (DCM). A reaction was performed at 0° C. for 24 hours using 130 μl of pyridine (10 mr) as a catalyst. Thereafter, a purification process was performed three times in cold ether to remove unreacted p-NPC and pyridine.

The above-mentioned manufacturing process is illustrated in the following reaction formula 1:

Measurement Example 1. $^1$H-NMR Analysis of p-NPC-Pluronic

Figure 1:
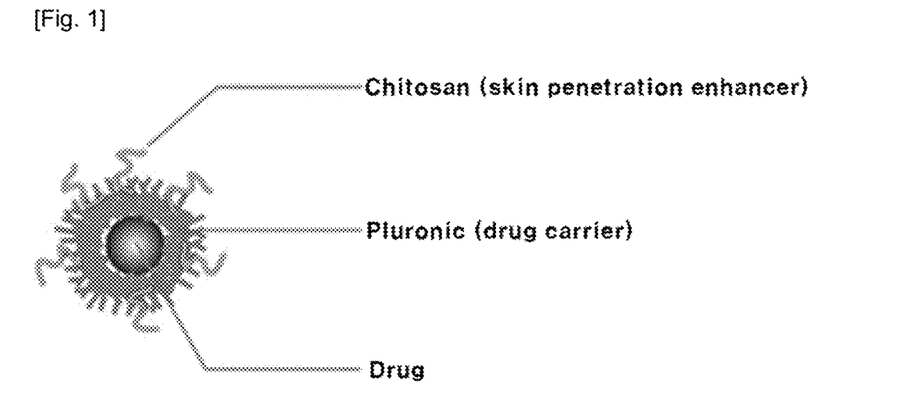
FIG. 1 is a schematic diagram of a nanocarrier according to an embodiment of the present disclosure.
Figure 2:
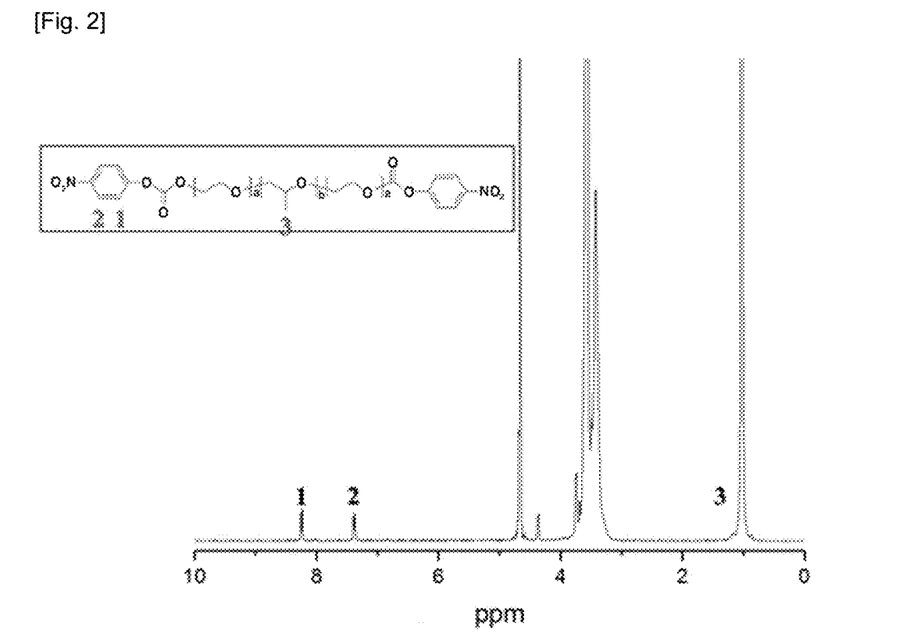
FIG. 2 is $^1$H-NMR analysis results of a reaction group-introduced pluronic polymer according to an embodiment of the present disclosure.

After freeze-drying a p-NPC-Pluronic polymer manufactured in the above-mentioned Example 1 in a powdery state, $^1$H-NMR was analyzed by dissolving the freeze-dried p-NPC-Pluronic polymer into D$_2$O. The $^1$H-NMR analysis results are illustrated in FIG. 2. Referring to FIG. 2, it can be confirmed that pyridine has completely been removed (substitution rate>98%, purity of 100%).

Example 2. Preparing Chitosan-Pluronic Complexes

(1) Example 2-1. Preparing a 3 kDa Chitosan-Pluronic Complex

After dissolving 300 mg of the p-NPC-Pluronic polymer in DMSO to substitute chitosan at both ends of a p-NPC-Pluronic polymer manufactured in the above-mentioned Example 1, a reaction process was performed at room temperature for 12 hours by adding 900 mg of 3 kDa chitosan along with triethylamine (TEA) as a catalyst to the p-NPC-Pluronic polymer dissolved in DMSO. Thereafter, in order to improve purity, unreacted chitosan was precipitated in acetone and removed, and unreacted TEA and p-NPC were removed from cold ether. Further, in order to improve purity, the impurity-removed chitosan-pluronic complex was freeze-dried in a powdery state after dialyzing the chitosan-pluronic complex in a deionized water, thereby removing impurities from the dialyzed chitosan-pluronic complex. The above-described preparation process is illustrated in the following reaction formula 2.

(2) Example 2-2. Preparing a 10 kDa Chitosan-Pluronic Complex

The 10 kDa chitosan-pluronic complex was prepared by the same method as in Example 2-1 except that 10 kDa chitosan was used.

[Reaction formula 1]

[Reaction formula 2]

Figure 3:
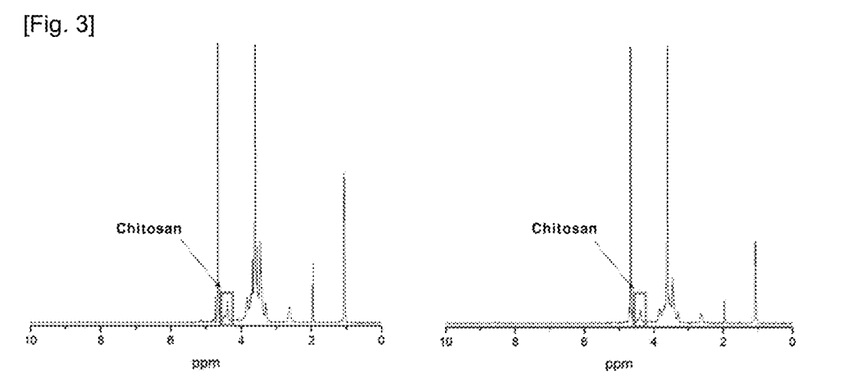
FIG. 3 is $^1$H-NMR analysis results of a chitosan-pluronic complex according to an embodiment of the present disclosure.

Measurement Example 2. $^1$H-NMR Analysis of Chitosan-Pluronic Complexes After performing a $^1$H-NMR analysis process by dissolving chitosan-pluronic complexes in a powdery state prepared in Examples 2-1 and 2-2 in $D_2O$, results of the process are shown in FIG. 3. Referring to FIG. 3 (a result of a left graph: using of 3 kDa chitosan (Example 2-1), a result of a right graph: using of 10 kDa chitosan (Example 2-2)), it can be confirmed that chitosan-pluronic complexes having a substitution rate of 98% or more irrespective of molecular weights of the chitosans can be prepared.

Example 3. Manufacturing Nanocarriers

Nanocarriers (3 kDa chitosan-substituted nanocarrier: $Chi_{3k}$-NS, 10 kDa chitosan-substituted nanocarrier: $Chi_{10k}$-NS)) were manufactured through nanoprecipitation by adjusting a ratio of the chitosan-pluronic complex prepared in Example 2 prepared in the above-mentioned Example 2 to pluronic. More specifically, after dissolving a 3 kDa or 10 kDa chitosan-substituted chitosan-pluronic complex prepared in the above-mentioned Example 2 and pluronic to a concentration of 10 mg/ml of acetone (99%, sigma aldrich) at weight ratio of 5:5, 8:2, and 10:0 to prepare mixed solutions, and slowing injecting 1 ml of the mixed solutions at a rate of 0.1 ml/min into 5 ml of deionized water that had been stirring at a rotation speed of 500 rpm, the mixed solutions were reacted with the deionized water at room temperature for 12 hours or more, and an acetone solvent was naturally evaporated and removed in the reaction process. The above-described manufacturing process is illustrated in the following reaction formula 3:

[Reaction formula 3]

Measurement Example 3. Measuring Sizes and Surface Charges of Nanocarriers

Figure 4:
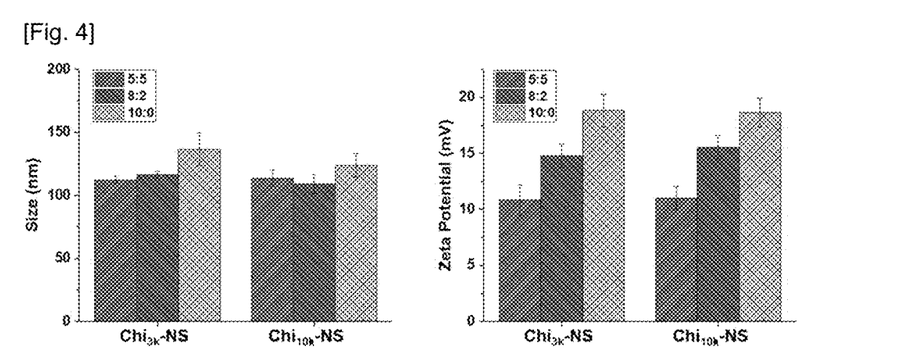
FIG. 4 is results of measuring sizes and surface charge values of a nanocarrier according to an embodiment of the present disclosure.

After filtering the nanocarriers manufactured in the above-mentioned Example 3 with a 0.2 μm syringe filter to obtain nanosponges, and analyzing sizes and surface charge values of 2 mg/ml of the nanosponges using DLS (ELS-8000, Otsuka Electronics Co., Japan) equipment, the analysis results are illustrated in FIG. 4.

Referring to FIG. 4, the manufactured nanocarriers show uniform distributions and sizes of 140 nm or less in all groups, and differences in sizes according to mixing ratios and molecular weights of chitosans are not shown to be great.

However, as results of measuring surface charge values, in case of formulations into which large amounts of chitosans are injected according to mixing ratios of the chitosan-pluronic complexes and pluronic, measured surface charge values shown higher positive charges (about +11 mV→about +18 mV), and differences in surface charge values according to the molecular weights of chitosans have not been observed.

Measurement Example 5. Measuring Chitosan Amounts on Surfaces of Nanocarriers A measurement process was performed using Ninhydin assay to quantitatively analyze chitosan amounts on surfaces of the nanocarriers manufactured in the above-mentioned Example 3. After mixing nanocarrier solutions with Ninhydrin reagents (2% solutions) at a volume ratio of 1:1 to obtain mixed solutions, the mixed solutions were reacted at a 90° C. condition for 30 minutes to obtain final reaction solutions. After quantitatively measuring amounts of chitosans by measuring 570 nm UV absorbance values of the final reaction solutions (violet), measurement results of the chitosan amounts are illustrated in FIG. 5.

Figure 5:
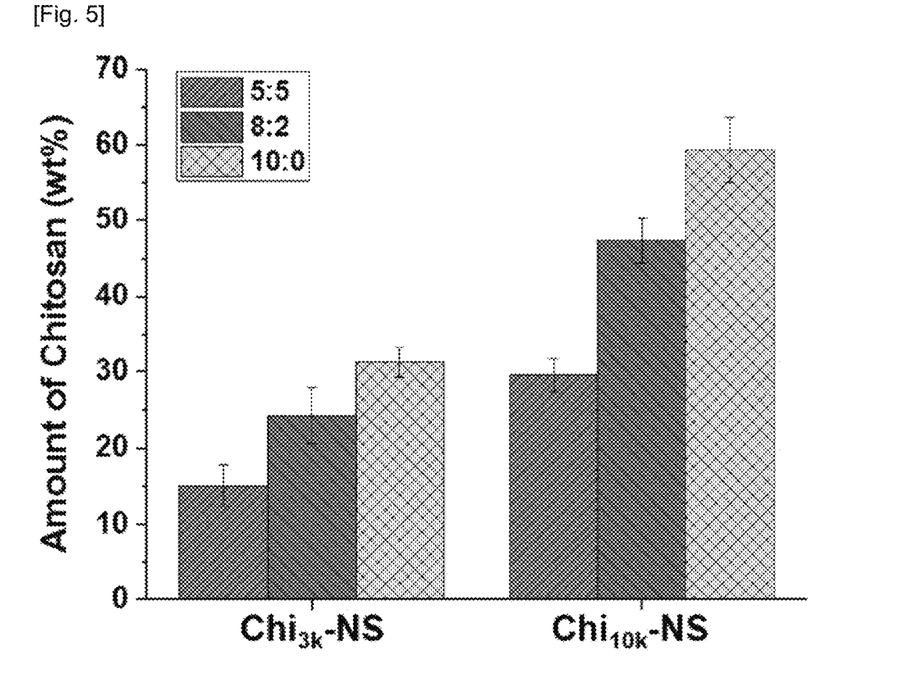
FIG. 5 is results of measuring amounts of chitosan on the surface of a nanocarrier according to an embodiment of the present disclosure.

Referring to FIG. 5, more amounts of chitosans exist in case of formulations into which more amounts of chitosans are injected according to mixing ratios.

Measurement Example 6. Stability Evaluation of Nanocarriers

Figure 6:
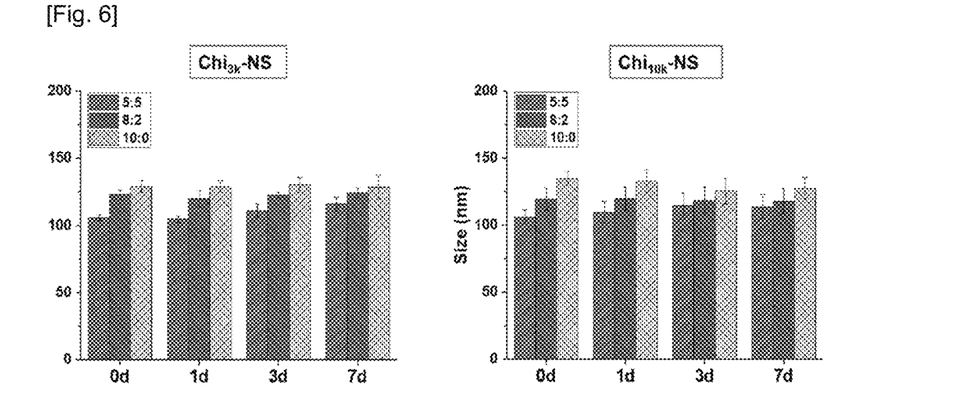
FIG. 6 is results of measuring stability values of a nanocarrier according to an embodiment of the present disclosure.

An analysis process was performed using DLS equipment to check if agglomeration phenomena of the nanocarriers were exhibited by time at conditions (PBS (pH 7.4), 37° C.) similar to an in vivo environment to evaluate stability of the nanocarriers manufactured in the above-mentioned Example 3. More specifically, after observing if stabilities of chitosans were maintained under conditions of 37° C. and 100 rpm for 7 days, observation results of the stabilities of chitosans are illustrated in FIG. 6. Referring to FIG. 6, it can be confirmed that the nanocarriers can be stable in the in vivo environment according as it is observed that the agglomeration phenomena are not exhibited, and uniform sizes of the nanocarriers are well maintained for 0 to 7 days.

Measurement Example 7. Evaluating Drug Loading Efficiencies and Characteristics of Drug-Loaded Nanocarriers The nanocarriers were loaded along with Nile red (ex.530 nm/em.635 nm) which had hydrophobic characteristics as a model drug and could exhibit red fluorescence when manufacturing nanocarriers. As results of analyzing loading efficiencies, about 95% of high loading efficiencies were exhibited.

Figure 7:
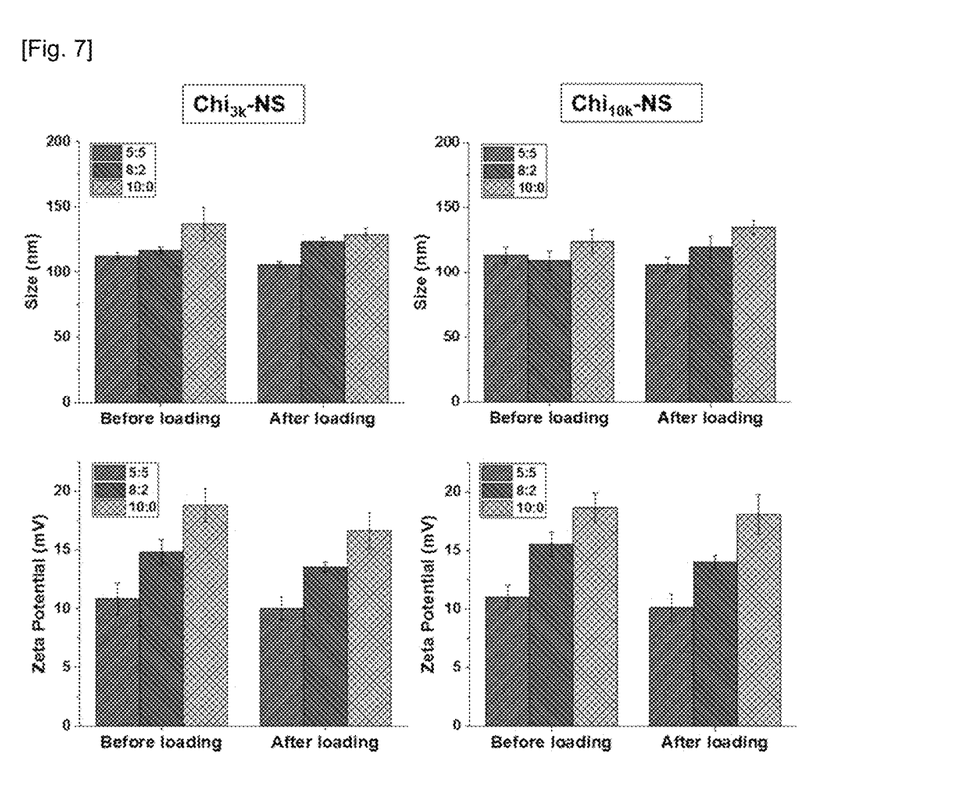
FIG. 7 is results of analyzing drug loading efficiencies of a nanocarrier according to an embodiment of the present disclosure.

After loading drugs, results of observing variations in sizes and surface charge values of the nanocarriers are illustrated in FIG. 7. Referring to FIG. 7, although a minute difference exists between sizes and surface charge values of the nanocarriers before and after loading the drugs in all conditions, there is not the difference statistically. Accordingly, it can be confirmed that the drugs are stably collected in hydrophobic polymer portions inside nanosponges.

Measurement Example 8. Evaluating Nanocarrier Cytotoxicity

After applying Mouse Embryonic fibrolast cell line (NIH/3T3, passage #15, 1×10$^4$ cells/wess) to 96 well cell culture plates, the 96 well cell culture plates having the Mouse Embryonic fibrolast cell line applied thereto were stabilized for about 12 hours (cell culture medium: DEMS including 10% of FBS and 1% of antibiotics)

After manufacturing nanocarriers having Nile red as a model drug loaded thereon in an amount of 1,000 μg/ml, adding the nanocarriers to cells, the nanocarriers added to the cells were cultured for 24 hours. After analyzing effects of the nanocarriers on cell metabolism in each group using WST-8 evaluation method, analysis results are illustrated in FIG. 8.

Figure 8:
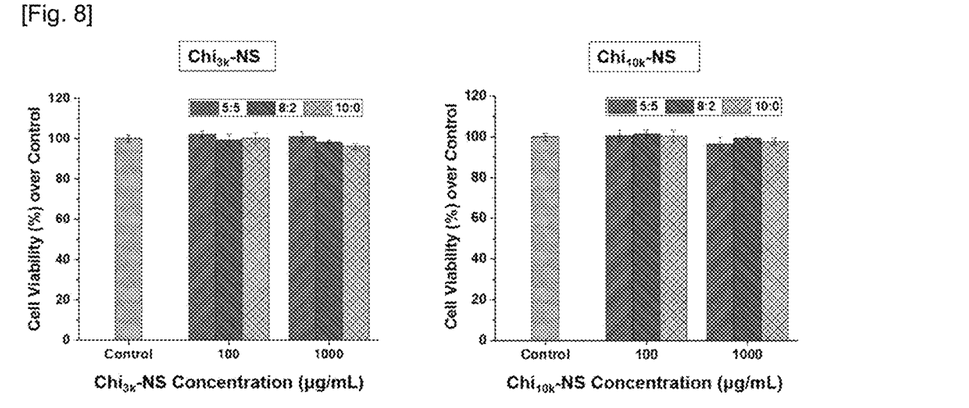
FIG. 8 is results of analyzing cytotoxicity values of a nanocarrier according to an embodiment of the present disclosure.

Referring to FIG. 8, it can be confirmed that the nanocarriers are excellent in bio compatibility without causing cytotoxicity up to the amount of 1,000 μg/ml in all conditions.

Measurement Example 9. Evaluating Skin Penetration Rates of Drugs

After injecting 5 ml of PBS, i.e., a release buffer into a receptor chamber of Franz type diffusion cell to experiment skin penetration of drugs, and covering human cadaver skin with a size of 1.5×1.5 cm$^2$ between the receptor chamber and a donor chamber, 2 mg/ml of each of samples (nanocarriers having a drug (Nile red) loaded thereon) was injected into a donor portion of Franz cell.

An analysis process was performed by measuring amounts of the drugs penetrating the skin after adjusting temperature and rotation speed of the receptor chamber to 37° C. and 600 rpm and recovering the drug-loaded nanocarriers as much as 500 μl for a sampling time of 0.5, 1, 2, 4, 8, 12, 18, or 24 hours.

Figure 9:
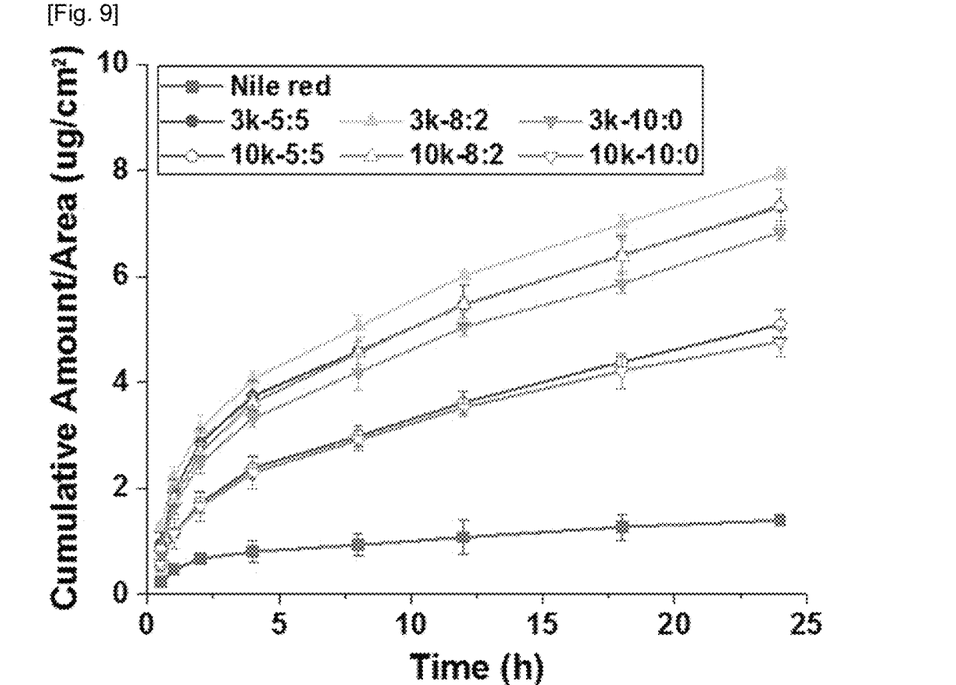
FIG. 9 is results of measuring skin penetration rate values of a drug using a nanocarrier according to an embodiment of the present disclosure.

Referring to FIG. 9, when nanocarrier formulations rather than control groups (drugs themselves) are used, it can be confirmed that skin penetration rates of the drugs are increased 4 times or more. Particularly, the highest skin penetration rates of the drugs were observed at formulations (3k-8:2) having the nanocarriers mixed with the chitosan at a ratio of 8:2 in nanocarriers substituted with 3 kDa chitosan's (skin penetration rates of the formulations (3k-8:2) were improved as much as about 8 times compared to the control groups).

Further, it can be confirmed that, in case of nanocarrier formulations using 3 kDa chitosan rather than nanocarrier formulations having the nanocarriers substituted with 10 kDa chitosan, it can be confirmed that molecular weight of chitosan may also have an effect on the skin penetration rates of the drugs according as skin penetration rates of drugs are improved.

After completing a skin penetration experiment of the drugs, skins were fixed in a 1-% neutral formalin solution for 12 hours or more to confirm how the drugs were distributed in the skins. After mixing the fixed skins with an OCT compound, allowing OCT compound-mixed skins to be frozen in liquid nitrogen of −20° C. or less, and cutting the frozen skins to a thickness of 20 μm through a cryo-section device (−25° C.), sampling was made by attaching the cut skins to glass. After washing samples with deionized water and observing distribution statuses of a model drug (Nile red) in the skins with a fluorescence microscope, observation results are illustrated in FIG. 10.

Figure 10:
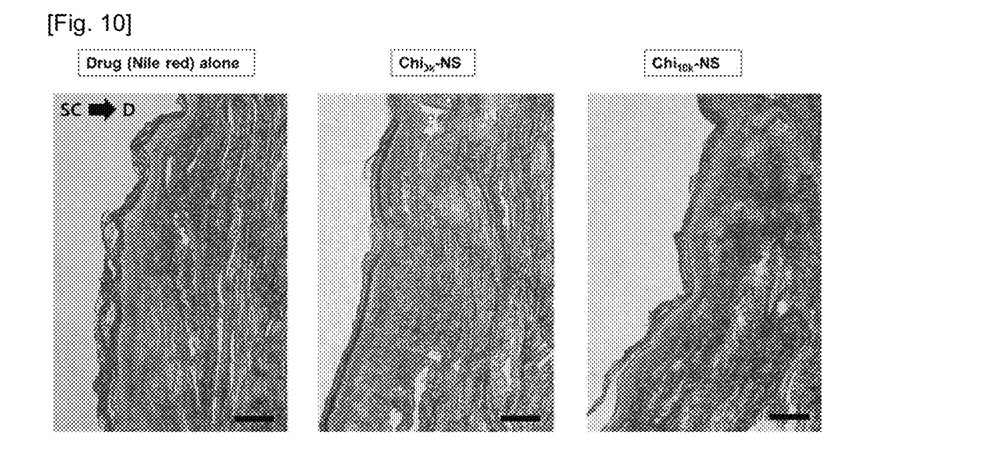
FIG. 10 is results of measuring skin penetration distribution images of a drug using a nanocarrier according to an embodiment of the present disclosure.

Referring to FIG. 10, it is observed that drugs having hydrophobicity and low molecular characteristics are collected in stratum corneum in a control group using a drug (Nile red) alone without using a nanocarrier, while it is observed that the drug is evenly spread to an epidermal layer and a dermal layer by permeating the stratum corneum in a group of using the nanocarrier.

Particularly, it has been confirmed that the formulations (Chi$_{3k}$-NS) can be used as a novel platform to deliver various incurable disease treating drugs into the skin according as a high amount of fluorescence is observed from a formulation (Chi$_{3k}$-NS) having the nanocarriers mixed with the 3 kDa chitosan at a ratio of 8:2, i.e., an optimal formulation condition.

As described above, the present disclosure has an effect of enabling a drug, a cosmetic material or the like to be efficiently delivered into the skin by providing a nanocarrier with improved skin penetration rate having its roots in a complex including chitosan.

Further, the present disclosure has an effect enabling the drug, the cosmetic material or the like to be stably delivered even in an in vivo environment by minimizing an agglomeration phenomenon of the nanocarrier.

Further, the present disclosure has an effect of providing a nanocarrier for transdermal penetration which has excellent bio compatibility since the nanocarrier does not cause cytotoxicity.

Although the present disclosure has been described along with the accompanying drawings, this is only one of various examples including the gist of the present disclosure and has an object of enabling a person having ordinary skill in the art to easily practice the invention. Accordingly, it is evident that the present disclosure is not limited to the aforementioned examples. Accordingly, the range of protection of the present disclosure should be interpreted based on the following claims, and all of technological spirits within the equivalents of the present disclosure may fall within the range of right of the present disclosure by changes, substitutions and replacements without departing from the gist of the present disclosure. Furthermore, it is evident that the configurations of some drawings have been provided to more clearly describe configurations and have been more exaggerated or reduced than actual configurations.

What is claimed is:

1. A nanocarrier for transdermal penetration comprising a chitosan-pluronic complex in which chitosan is substituted at both ends of a pluronic polymer, and further comprising a pluronic polymer, wherein the chitosan-substituted pluronic polymer is represented by the following chemical formula 1, (PEO)$a$-(PPO)$b$-(PEO)$a$      [Chemical Formula 1]

wherein the PEO is polyethylene oxide, the PPO is polypropylene oxide, and the a and b are each independently an integer of 1 to 300, and wherein a weight ratio of the chitosan-pluronic complex and the pluronic polymer further comprised in the nanocarrier is 8:2.

2. The nanocarrier of claim 1, wherein the chitosan-pluronic complex includes chitosan having a molecular weight of 3 to 760 kDa.

3. The nanocarrier of claim 1, wherein the nanocarrier has a size of 500 nm or less.

4. The nanocarrier of claim 1, wherein the nanocarrier has a surface charge value of 0 to 50 mV.

5. The nanocarrier of claim 1, wherein the nanocarrier has a loading efficiency of 90% or more for Nile red.

6. The nanocarrier of claim 1, wherein the nanocarrier is a nanocarrier for transdermal penetration or oral administration.

7. A method of manufacturing the nanocarrier for transdermal penetration according to claim 1, the method comprising the steps of:
(a) mixing a pluronic polymer with chitosan to prepare a complex in which chitosan is substituted at an end of the pluronic polymer;
(b) mixing the complex with the pluronic polymer in the presence of a solvent to prepare a mixture;
(c) dropping the mixture on distilled water; and
(d) stirring the mixture-dropped distilled water.

8. The method of claim 7, wherein the step (a) comprises mixing chitosan with a molecular weight of 3 to 760 kDa.

* * * * *